United States Patent
Yokoi et al.

(10) Patent No.: US 7,211,406 B2
(45) Date of Patent: May 1, 2007

(54) POTASSIUM CHANNEL

(75) Inventors: Hiromichi Yokoi, Ibaraki (JP); Kohei Inamura, Ibaraki (JP); Yorikata Sano, Ibaraki (JP); Akira Miyake, Ibaraki (JP); Shinobu Mochizuki, Ibaraki (JP)

(73) Assignee: Astellas Pharms Inc., Tokyo (JP)

( * ) Notice: Subject to any disclaimer, the term of this patent is extended or adjusted under 35 U.S.C. 154(b) by 0 days.

(21) Appl. No.: 10/451,892

(22) PCT Filed: Dec. 26, 2001

(86) PCT No.: PCT/JP01/11458

§ 371 (c)(1),
(2), (4) Date: Jun. 26, 2003

(87) PCT Pub. No.: WO02/053730

PCT Pub. Date: Jul. 11, 2002

(65) Prior Publication Data

US 2004/0029804 A1    Feb. 12, 2004

(30) Foreign Application Priority Data

Dec. 27, 2000  (JP) ............................. 2000-398521
Apr. 11, 2001  (JP) ............................. 2001-113131

(51) Int. Cl.
*G01N 33/566* (2006.01)
*C07K 14/705* (2006.01)
*C07H 21/04* (2006.01)
*C12N 15/11* (2006.01)
*C12N 5/16* (2006.01)

(52) U.S. Cl. ............... 435/7.21; 435/7.2; 435/252.3; 435/254.2; 435/320.1; 435/348; 435/357; 435/358; 435/365; 435/369; 530/350; 536/23.5

(58) Field of Classification Search ............... 514/12; 530/350; 435/7.1, 69.1, 320.1, 325; 536/23.2
See application file for complete search history.

(56) References Cited

U.S. PATENT DOCUMENTS

2004/0072216 A1* 4/2004 Johnson et al. ............... 435/6

FOREIGN PATENT DOCUMENTS

| JP | 2002-233369 A | 8/2002 |
| WO | WO 00/52164 | 9/2000 |
| WO | WO 02/12340 A2 | 2/2002 |
| WO | WO 200212340 A2 * | 2/2002 |
| WO | WO 02/088378 A2 | 11/2002 |

OTHER PUBLICATIONS

Han, et al. Apr. 30, 2003. Functional properties of four splice variants of a human pancreatic tandem-pore K+ channel, TALK-1. Am J Physiol Cell Physiol. 285: C529-C538.*

Goldstein, et al. Mar. 2001. Potassium Leak Channels and the KCNK Family of Two-P-Domain Subunits. Nature Reviews Neuroscience. 2: 175-184.*

Kang, et al. 2004. Functional expression of TREK-2 in insulin-secreting MIN6 cells. Biochemical and Biophysical Research Communications. 323:323-331.*

Duprat et al. Oct. 28, 2004. Pancreatic Two P Domain K+ Channels TALK-1 and TALK-2 are activated by Nitric Oxide and Reactive Oxygen Species. J Physiol. Epub ahead of print. Abstract Only.*

Logan et al. Jul. 1994, Cystic Fibrosis Transmembrane Conductance Regulator Mutations That Disrupt Nucleotide Binding. J Clin Invest. 94:228-236.*

Lehninger et al. 1993. Principles of Biochemistry. John Wiley & Sons Inc. p. 187.*

Yan et al. 2000. Two-amino acid molecular switch in an epithelial morphogen that regulates binding to two distinct receptors. Science 290: 523-527.*

Wells (Sep. 18, 1990) Biochemistry 29(37): 8509-8517.*

Ngo et al. (Mar. 2, 1995) "The Protein Folding Problem and Tertiary Structure Prediction, Chapter 14: Computational Complexity Protein Structure Prediction, and the Levinthal Paradox" pp. 492-495.*

Bork (2000) *Genome Research* 10:398.*

Skolnick and Fetrow (2000) *Trends in Biotech*. 18(1): 34.*

Doerks et al. (Jun. 1998) *Trends in Genetics* 14(6): 248.*

Smith and Zhang (Nov. 1997) *Nature Biotechnology* 15:1222.*

Brenner (Apr. 1999) *Trends in Genetics* 15(4): 132.*

Bork and Bairoch (Oct. 1996) *Trends in Genetics* 12(10): 425.*

Duprat et al. Oct. 28, 2004. J Physiol. 562.1: 235-244.*

Kang et al, 2004, Biochemical and Biophysical Research Communication. 323: 323-331.*

Mears et al, 2004. J. Membrane Biol. 200: 57-66.*

Ozaita et al, 2002. Molecular Brain Research. 102: 18-27.*

Kang et al, 2004. Biochemical and Biophysical Research Communications. 315: 836-844.*

Lesage et al. (2000) "Molecular and functional properties of two-pore-domain potassium channels," *Am. J. Physiol.: Renal Fluid and Electrolyte Phys.*, 279:F793-F801.

(Continued)

*Primary Examiner*—Elizabeth Kemmerer
*Assistant Examiner*—Zachary C. Howard
(74) *Attorney, Agent, or Firm*—Finnegan, Henderson, Farabow, Garrett, & Dunner, LLP

(57) ABSTRACT

A novel polypeptide which is useful in searching for a therapeutic agent for diabetes, a polynucleotide encoding the polypeptide, an expression vector comprising the polynucleotide, a cell transfected with the expression vector, an antibody binding to the polypeptide, and a method of screening a therapeutic agent for diabetes are disclosed.

The polypeptide is a novel background potassium channel expressed in the pancreas.

7 Claims, 1 Drawing Sheet

OTHER PUBLICATIONS

Williams; "Direct Submission"; Sequence Database, Accession No. AL136087, Sanger Centre, Hinxton, Cambridgeshire, CB10 1SA, United Kingdom, pp. 1-47, (2000).

Girard et al.; "Genomic and Functional Characteristics of Novel Human Pancreatic 2P Domain K$^+$Channels"; Biochemical and Biophysical Reasearch Communications, vol. 282, No. 1, pp. 249-256, (2001).

Rudy, "Diversity and ubiquity of K channels," *Neuroscience*, 25(3):729-749 (1988).

Han et al., "Functional properties of four splice variants of a human pancreatic tandem-pore K$^+$channel, TALK-1," *Am. J. Physiol. Cell Physiol.*, 285:C529-C538 (2003).

\* cited by examiner (A) 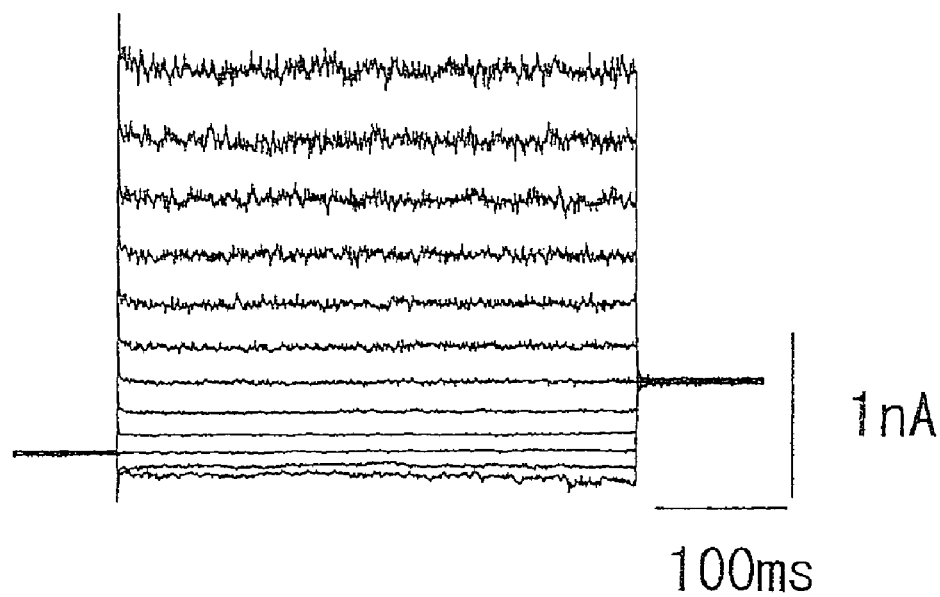
(B) 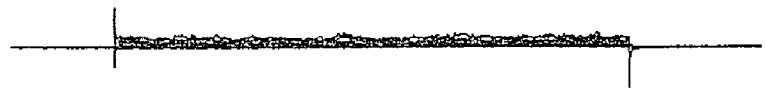

POTASSIUM CHANNEL

TECHNICAL FIELD

This invention relates to a novel potassium channel.

BACKGROUND ART

The pancreas secretes insulin, as a blood glucose regulatory hormone, from β cells in accordance with a blood glucose level, and regulates blood glucose. A deficiency of an insulin action causes chronic hyperglycemia, and diabetes accompanied by various characteristic metabolic disorders.

Glucose incorporated into β cells is metabolized to generate various metabolites such as ATP. An ATP sensitive potassium ($K^+$) channel ($K_{ATP}$ channel) exists in the β cell. When the $K_{ATP}$ channel is closed by ATP generated by the glucose metabolism, a depolarization of a cell membrane, an activation of a voltage-gated calcium ($Ca^{2+}$) channel, and an increase of an intracellular $Ca^{2+}$ concentration occur, and then insulin secretory granules are released.

The $K_{ATP}$ channel does not function unless eight subunits, i.e., four Kir6.2 subunits and four SUR (Sulphonylurea receptor) subunits, are assembled to construct a channel structure. The $K_{ATP}$ channel subunit Kir6.2 is expressed in the pancreas, brain, cardiac muscle, skeletal muscle, and the like, and a complex of Kir6.2 and SUR1 (Sulphonylurea receptor 1) is formed in the pancreas (Inagaki N., Science, 270, 1166–1170, 1995; and Seino S., Diabetes, 49, 311–318, 2000).

In a dominant-negative transgenic mouse with respect to Kir6.2, an increase of a resting membrane potential in pancreatic β cells and an increase of intracellular calcium ion concentration are observed, hyperinsulinism and hypoglycemia are observed (Miki, Proc. Natl. Acad. Sci. USA, 94, 11969–11973).

$K_{ATP}$ channel inhibitors cause a depolarization of the cell membrane in β cells, and promote insulin secretion. One of the most popular inhibitors is an SU (Sulphonyl urea) agent which binds to the SUR1 subunit. However, it is known that the SU agent has a problem of secondary failure due to an exhaustion of pancreatic β cells (Groop L., Am. J. Med., 87, 183–190, 1989; Shigeta, Tonyobyo-chiryo-jiten (Dictionary of diabetes treatment), Igaku-syoin, 1996).

In type II diabetes, insulin secretion by a glucose stimulation is generally decreased. However, according to a study using a whole cell recording of patch-clamp methods, in a GK rat as a nonobese type II diabetes model rat (nonobese type II diabetes model obtained by selective breeding of a Wistar rat using a glucose tolerance test as a marker), an activation of a voltage-dependent $Ca^{2+}$ channel by a depolarization stimulation was induced by comparison with a control (Kato S., J. Clin Invest., 97, 2417–2425, 1996). Further, according to a study using pancreatic islet's of Langerhans treated by a electropermeabilization method, in the GK rat, a sensitivity of secretory granule-releasing system against an increase of an intracellular $Ca^{2+}$ concentration was induced (Okamoto Y., Diabetologia, 38, 772–778, 1995). Therefore, it is considered that, in type II diabetes, the secretion is maintained or induced with respect to depolarization stimulations other than glucose.

DISCLOSURE OF INVENTION

The object of the present invention is to provide a convenient screening system and a screening tool to obtain a substance useful as a therapeutic agent for diabetes in which the mechanism is an increase in the excitation of pancreatic β cells and a promotion of insulin secretion.

The present inventors have conducted intensive studies and, as a result, obtained a human polynucleotide encoding an amino acid sequence of SEQ ID NO: 2 and significantly expressed in the pancreas, and then obtained rat or mouse polynucleotide corresponding to the human polynucleotide. Further, these polynucleotides were expressed, the present inventors confirmed that the polypeptides encoded by the polynucleotides exhibited properties of a background potassium channel, and a tool useful in screening a therapeutic agent for diabetes, particularly an agent for promoting insulin secretion, was provided. Furthermore, the present inventors constructed a system for conveniently detecting the potassium channel activity, and provided a convenient method of screening a therapeutic agent for diabetes, particularly an agent for promoting insulin secretion, and the present invention was completed.

Accordingly, the present invention relates to:

[1] (1) a polypeptide comprising an amino acid sequence of SEQ ID NO: 2, SEQ ID NO: 6, or SEQ ID NO: 10 and exhibiting a background potassium channel activity, or (2) a polypeptide exhibiting a background potassium channel activity and comprising an amino acid sequence in which 1 to 10 amino acids are substituted, deleted, and/or inserted in an amino acid sequence of SEQ ID NO: 2, SEQ ID NO: 6, or SEQ ID NO: 10;

[2] a polypeptide exhibiting a background potassium channel activity and comprising an amino acid sequence having a 90% or more homology with that of SEQ ID NO: 2, SEQ ID NO: 6, or SEQ ID NO: 10;

[3] a polypeptide comprising an amino acid sequence of SEQ ID NO: 2, SEQ ID NO: 6, or SEQ ID NO: 10 and exhibiting a background potassium channel activity;

[4] a polypeptide consisting of an amino acid sequence of SEQ ID NO: 2, SEQ ID NO: 6, or SEQ ID NO: 10;

[5] a polynucleotide encoding the polypeptide of [1] to [4];

[6] an expression vector comprising the polynucleotide of [5];

[7] a cell transfected with the expression vector of [6];

[8] an antibody or a fragment thereof, which binds to the polypeptide of [1] to [4];

[9] a method for detecting whether or not a test compound suppresses the polypeptide of [1] to [4], comprising the steps of:

bringing the cell of [7] into contact with the test compound, and analyzing whether or not the polypeptide is suppressed; and

[10] a method of screening a therapeutic agent for diabetes, comprising a detecting step by the method of [9].

BRIEF DESCRIPTION OF DRAWINGS

FIG. 1 is a graph showing the result of an observation of an outward current induced when a depolarization pulse was given to an L929 cell transfected with a plasmid pIRESneo2-hPSI (A) or a control vector (B) while voltage-clamping by a whole-cell voltage-clamp method.

BEST MODE FOR CARRYING OUT THE INVENTION

The present invention will be explained in detail hereinafter.

[1] The Polypeptide of the Present Invention

The polypeptide of the present invention includes (1) a polypeptide comprising the amino acid sequence of SEQ ID NO: 2, SEQ ID NO: 6, or SEQ ID NO: 10;

(2) a polypeptide exhibiting a background potassium channel activity and comprising an amino acid sequence in which one or plural amino acids in total are substituted, deleted, and/or inserted at one or plural positions in the amino acid sequence of SEQ ID NO: 2, SEQ ID NO: 6, or SEQ ID NO: 10 (hereinafter referred to as a variation functionally equivalent); and (3) a polypeptide exhibiting a background potassium channel activity and comprising an amino acid sequence having a 90% or more homology with that of SEQ ID NO: 2, SEQ ID NO: 6, or SEQ ID NO: 10 (hereinafter referred to as a homologous polypeptide).

The "polypeptide comprising the amino acid sequence of SEQ ID NO: 2, SEQ ID NO: 6, or SEQ ID NO: 10" as the polypeptide of the present invention is not particularly limited, so long as it is a polypeptide comprising the amino acid sequence of SEQ ID NO: 2, SEQ ID NO: 6, or SEQ ID NO: 10 and exhibiting a background potassium channel activity. It includes, for example, the polypeptide consisting of the amino acid sequence of SEQ ID NO: 2;

the polypeptide consisting of the amino acid sequence of SEQ ID NO: 6;

the polypeptide consisting of the amino acid sequence of SEQ ID NO: 10;

a fusion polypeptide exhibiting a background potassium channel activity and consisting of an amino acid sequence in which an appropriate marker sequence or the like is added to the N-terminus and/or the C-terminus of the polypeptide consisting of the amino acid sequence of SEQ ID NO: 2;

a fusion polypeptide exhibiting a background potassium channel activity and consisting of an amino acid sequence in which an appropriate marker sequence or the like is added to the N-terminus and/or the C-terminus of the polypeptide consisting of the amino acid sequence of SEQ ID NO: 6; and a fusion polypeptide exhibiting a background potassium channel activity and consisting of an amino acid sequence in which an appropriate marker sequence or the like is added to the N-terminus and/or the C-terminus of the polypeptide consisting of the amino acid sequence of SEQ ID NO: 10.

The polypeptide consisting of the amino acid sequence of SEQ ID NO: 2, one of the polypeptides of the present invention, is a novel human background potassium channel protein consisting of 294 amino acid residues. The polypeptide consisting of the amino acid sequence of SEQ ID NO: 2 is a protein which is significantly expressed in the pancreas as shown in Example 4.

The polypeptide consisting of the amino acid sequence of SEQ ID NO: 6 is a novel rat background potassium channel protein consisting of 292 amino acid residues.

The polypeptide consisting of the amino acid sequence of SEQ ID NO: 10 is a novel mouse background potassium channel protein consisting of 292 amino acid residues.

A genome draft sequence is disclosed in AL136087 registered in GenBank, and CDS's deduced in the genome and deduced amino acid sequences are also described. One of the deduced amino acid sequences is the same as that of SEQ ID NO: 2. However, as described "evidence=not experimental" in the database, neither the polynucleotide consisting of the base sequence of SEQ ID NO: 1 nor the polypeptide consisting of the amino acid sequence of SEQ ID NO: 2 is obtained. In addition, the database does not disclose a method for preparing the polypeptide consisting of the amino acid sequence of SEQ ID NO: 2, an expression distribution of the present channel (i.e., the channel of the present invention) in tissues, and its roles in the body, and does not suggest that the present channel can be used for screening a therapeutic agent for diabetes.

Further, in Girard, C., Biochem. Biophys. Res. Commun., 282, 249–256 (2001) March 23rd published after the priority date of the present application, a background potassium channel TALK-1 exclusively expressed in the pancreas, having an amino acid sequence in which 271 amino acid residues in the amino acid sequence (number of amino acid residues 294) of SEQ ID NO: 2 are identical, is described. However, its roles are unclear, and it is not disclosed that the present channel can be used for screening a therapeutic agent for diabetes, and that insulin secretion is suppressed by suppressing the present channel.

As the marker sequence in the polypeptide of the present invention, a sequence for easily carrying out a confirmation of polypeptide expression, a confirmation of intracellular localization thereof, a purification thereof, or the like may be used. As the sequence, there may be mentioned, for example, a FLAG tag, a hexa-histidine tag, a hemagglutinin tag, a myc epitope, or the like.

The term "exhibiting a background potassium channel activity" as used herein means that three features, i.e., (a) that a current is generated by a voltage stimulus;

(b) that the current generated by the voltage stimulus is instantaneously induced and is not inactivated; and (c) that the selectivity of a potassium ion is high, are met (Duprat, EMBO J., 16, 5464, 1997; or Lesage and Lazdunski, Am. J. Physiol. Renal. Physiol., 279, F793, 2000).

Whether or not "a current is generated by a voltage stimulus" in a polypeptide (hereinafter referred to as a test polypeptide), and whether or not "a current is instantaneously induced and is not inactivated" in the test polypeptide as used herein may be confirmed by a method known to those skilled in the art (Hille, B., Ionic Channels of Excitable Membranes, 2nd Ed., Sinauer Associates Inc., MA, 1992). A method for confirming this is not particularly limited but, for example, the following method (preferably a method described in Example 6) may be used. More particularly, a cell is transfected with an expression vector comprising a polynucleotide encoding the test polypeptide, and a depolarization pulse of 0 mV from a holding potential of −80 mV for 400 msec is given to the resulting cell while voltage-clamping by a whole-cell voltage-clamp method. When an outward current is generated by the depolarization pulse, it may be confirmed that "a current is generated by a voltage stimulus" in the test polypeptide. When the outward current generated by the depolarization pulse is instantaneously induced and is not inactivated, it may be confirmed that "a current is instantaneously induced and is not inactivated" in the test polypeptide.

Whether or not "the selectivity of a potassium ion is high" in the test polypeptide as used herein may be confirmed by a method known to those skilled in the art (Hille, B., Ionic Channels of Excitable Membranes, 2nd Ed., Sinauer Associates Inc., MA, 1992). A method for confirming it is not particularly limited, but for example the following method (preferably a method described in Example 7) may be used. More particularly, a cell is transfected with an expression vector comprising a polynucleotide encoding the test polypeptide, and then the resulting cell is voltage-clamped by a whole-cell voltage-clamp method. While changing a potassium ion concentration in the extracellular solution, a reversal potential in each potassium ion concentration is measured using a voltage ramp. The reversal potential in each potassium ion concentration is plotted. When the slope of the resulting line is close to the theoretical value (preferably 47 to 58 mV/decade) of slope calculated from Nernst's equation:

$$E=(2.303RT/F)\log([K]out/[K]in)$$

(wherein E is a membrane potential, [K]out is a concentration of an extracellular potassium ion, [K]in is a concentration of an intracellular potassium ion, R is the gas constant, F is the Faraday constant, and T is an absolute temperature), it may be confirmed that "the selectivity of a potassium ion is high" in the test polypeptide.

The variation functionally equivalent of the present invention is not particularly limited, so long as it is a polypeptide exhibiting the background potassium channel activity and comprising an amino acid sequence in which one or plural (preferably 1 to 10, more preferably 1 to 7, most preferably 1 to 5) amino acids in total (for example, one or several amino acids in total) are deleted, substituted, and/or inserted at one or plural positions in the amino acid sequence of SEQ ID NO: 2, SEQ ID NO: 6, or SEQ ID NO: 10. Further, an origin of the variation functionally equivalent is not limited to a human, a rat, or a mouse.

The variation functionally equivalent of the present invention includes, for example, not only human variations of the polypeptide consisting of the amino acid sequence of SEQ ID NO: 2, rat variations of the polypeptide consisting of the amino acid sequence of SEQ ID NO: 6, or mouse variations of the polypeptide consisting of the amino acid sequence of SEQ ID NO: 10, but also variations functionally equivalent derived from organisms other than a human, a rat, or a mouse (such as a hamster or a dog). Further, it includes polypeptides prepared using polynucleotides obtained by artificially modifying their amino acid sequences encoded thereby by genetic engineering techniques, on the basis of polynucleotides encoding these native polypeptides (i.e., human, rat, or mouse variations or variations functionally equivalent derived from organisms other than a human, a rat, or a mouse), or on the basis of polynucleotides encoding an amino acid sequence represented by the amino acid sequence of SEQ ID NO: 2, SEQ ID NO: 6, or SEQ ID NO: 10. The term "variation" as used herein means an individual difference between the same polypeptides in the same species or a difference between homologous polypeptides in several species. As the variation functionally equivalent of the present invention, there may be mentioned, for example, a polypeptide consisting of the amino acid sequence of SEQ ID NO: 10, which consists of an amino acid sequence in which six amino acids are substituted in the amino acid sequence of SEQ ID NO: 6.

Human variations of the polypeptide consisting of the amino acid sequence of SEQ ID NO: 2, rat variations of the polypeptide consisting of the amino acid sequence of SEQ ID NO: 6, or mouse variations of the polypeptide consisting of the amino acid sequence of SEQ ID NO: 10, or variations functionally equivalent derived from organisms other than a human, a rat, or a mouse may be obtained by those skilled in the art in accordance with the information of a base sequence (for example, a sequence consisting of the 13th to 897th bases in the base sequence of SEQ ID NO: 1, a sequence consisting of the 36th to 914th bases in the base sequence of SEQ ID NO: 5, or a sequence consisting of the 1st to 879th bases in the base sequence of SEQ ID NO: 9) of a polynucleotide encoding the polypeptide consisting of the amino acid sequence of SEQ ID NO: 2, SEQ ID NO: 6, or SEQ ID NO: 10. In this connection, genetic engineering techniques may be performed in accordance with known methods (for example, Maniatis, T. et al., "Molecular Cloning—A Laboratory Manual", Cold Spring Harbor Laboratory, NY, 1982), unless otherwise specified.

For example, an appropriate probe or appropriate primers are designed in accordance with the information of a base sequence of a polynucleotide encoding the polypeptide consisting of the amino acid sequence of SEQ ID NO: 2, SEQ ID NO: 6, or SEQ ID NO: 10. A polymerase chain reaction (PCR) method (Saiki, R. K. et al., Science, 239, 487–491, 1988) or a hybridization method is carried out using a sample (for example, total RNA or an mRNA fraction, a cDNA library, or a phage library) prepared from an organism (for example, a mammal such as a human, a mouse, a rat, a hamster, or a dog) of interest and the primers or the probe to obtain a polynucleotide encoding the polypeptide. A desired polypeptide may be obtained by expressing the resulting polynucleotide in an appropriate expression system, and then, for example, by confirming that a current is generated by a depolarization pulse and the current is instantaneously induced and is not inactivated in the expressed polypeptide by a method described in Example 6, and further confirming that the selectivity of a potassium ion is high by a method described in Example 7.

Further, the polypeptide artificially modified by genetic engineering techniques may be obtained by, for example, the following procedure. A polynucleotide encoding the polypeptide is obtained by a conventional method such as site-directed mutagenesis (Mark, D. F. et al., Proc. Natl. Acad. Sci. USA, 81, 5662–5666, 1984). A desired polypeptide may be obtained by expressing the resulting polynucleotide in an appropriate expression system, and then, for example, by confirming that a current is generated by a depolarization pulse and the current is instantaneously induced and is not inactivated in the expressed polypeptide by a method described in Example 6, and further confirming that the selectivity of a potassium ion is high by a method described in Example 7.

The variation functionally equivalent of the present invention includes a fusion polypeptide exhibiting a background potassium channel activity and consisting of an amino acid sequence in which an appropriate marker sequence or the like is added to the N-terminus and/or the C-terminus of an amino acid sequence in which one or plural (preferably 1 to 10) amino acids are deleted, substituted, and/or inserted at one or plural positions in the amino acid sequence of SEQ ID NO: 2, SEQ ID NO: 6, or SEQ ID NO: 10.

The homologous polypeptide of the present invention is not particularly limited, so long as it is a polypeptide exhibiting the background potassium channel activity and comprising an amino acid sequence having a 90% or more homology with that of SEQ ID NO: 2, SEQ ID NO: 6, or SEQ ID NO: 10. As the homologous polypeptide of the present invention, a polypeptide exhibiting the background potassium channel activity and comprising an amino acid sequence having more preferably a 95% or more homology, still further preferably a 98% or more homology, most preferably a 99% or more homology, with respect to the amino acid sequence of SEQ ID NO: 2, SEQ ID NO: 6, or SEQ ID NO: 10, is preferable. As the homologous polypeptide having a 90% or more homology with the amino acid sequence of SEQ ID NO: 6, there may be mentioned, for example, a polypeptide consisting of the amino acid sequence of SEQ ID NO: 10.

The term "homology" as used herein means a value obtained by a Clustal program (Higgins and Sharp, Gene, 73, 237–244, 1988; and Thompson, Nucleic Acid Res., 22, 4673–4680, 1994) using a default parameter. The default parameter is as follows:
As Pairwise Alignment Parameters,
K tuple 1
Gap Penalty 3
Window 5
Diagonals Saved 5.

As above, the polypeptide of the present invention is explained, but as the polypeptide of the present invention,
the polypeptide consisting of the amino acid sequence of SEQ ID NO: 2;
the polypeptide consisting of the amino acid sequence of SEQ ID NO: 6;
the polypeptide consisting of the amino acid sequence of SEQ ID NO: 10;
a polypeptide exhibiting the background potassium channel activity and consisting of an amino acid sequence in which 1 to 10 (preferably 1 to 7, more preferably 1 to 5) amino acids in total (for example, one or several amino acids in total) are deleted, substituted, inserted, and/or added at one or plural positions in the amino acid sequence of SEQ ID NO: 2, SEQ ID NO: 6, or SEQ ID NO: 10; or
a polypeptide exhibiting the background potassium channel activity and consisting of an amino acid sequence having a 90% or more homology (more preferably a 95% or more homology, still further preferably a 98% or more homology, most preferably a 99% or more homology) with that of SEQ ID NO: 2, SEQ ID NO: 6, or SEQ ID NO: 10
is preferable, and
the polypeptide consisting of the amino acid sequence of SEQ ID NO: 2;
the polypeptide consisting of the amino acid sequence of SEQ ID NO: 6; or
the polypeptide consisting of the amino acid sequence of SEQ ID NO: 10
is more preferable.

[2] The Polynucleotide of the Present Invention

The polynucleotide of the present invention is not particularly limited, so long as it encodes the polypeptide of the present invention. There may be mentioned, for example,
the polynucleotide consisting of the sequence consisting of the 13th to 897th bases in the base sequence of SEQ ID NO: 1;
the polynucleotide consisting of the sequence consisting of the 36th to 914th bases in the base sequence of SEQ ID NO: 5; or
the polynucleotide consisting of the sequence consisting of the 1st to 879th bases in the base sequence of SEQ ID NO: 9.

In this connection, the term "polynucleotide" as used herein includes both DNA and RNA.

A method for producing the polynucleotide of the present invention is not particularly limited, but there may be mentioned, for example, (1) a method using PCR, (2) a method using conventional genetic engineering techniques (i.e., a method for selecting a transformant comprising a desired cDNA from strains transformed with a cDNA library), or (3) a chemical synthesis method. These methods will be explained in this order hereinafter.

In the method using PCR of the item (1), the polynucleotide of the present invention may be produced, for example, by the following procedure.

mRNA is extracted from human cells or tissue capable of producing the polypeptide of the present invention. A pair of primers, between which full-length mRNA corresponding to the polypeptide of the present invention or a partial region of the mRNA is located, is synthesized on the basis of the base sequence of a polynucleotide encoding the polynucleotide of the present invention. Full-length cDNA encoding the polypeptide of the present invention or a part of the cDNA may be obtained by performing a reverse transcriptase-polymerase chain reaction (RT-PCR) using the extracted mRNA as a template.

More particularly, total RNA containing mRNA encoding the polypeptide of the present invention is extracted by a known method from cells or tissue capable of producing the polypeptide of the present invention. As an extraction method, there may be mentioned, for example, a guanidine thiocyanate-hot phenol method, a guanidine thiocyanate-guanidine hydrochloride method, or a guanidine thiocyanate-cesium chloride method. The guanidine thiocyanate-cesium chloride method is preferably used. The cells or tissue capable of producing the polypeptide of the present invention may be identified, for example, by a northern blotting method using a polynucleotide or a part thereof encoding the polypeptide of the present invention or a western blotting method using an antibody specific for the polypeptide of the present invention.

Next, the extracted mRNA is purified. Purification of the mRNA may be made in accordance with a conventional method. For example, the mRNA may be purified by adsorption and elution using an oligo(dT)-cellulose column. The mRNA may be further fractionated by, for example, a sucrose density gradient centrifugation, if necessary. Alternatively, commercially available extracted and purified mRNA may be used without carrying out the extraction of the mRNA.

Next, the first-strand cDNA is synthesized by carrying out a reverse transcriptase reaction of the purified mRNA in the presence of a random primer, an oligo dT primer, and/or a custom primer. This synthesis may be carried out in accordance with a conventional method. The resulting first-strand cDNA is subjected to PCR using two primers between which a full-length or a partial region of the polynucleotide of interest is located, thereby amplifying the cDNA of interest. The resulting DNA is fractionated by, for example, an agarose gel electrophoresis. The DNA fragment of interest may be obtained by carrying out a digestion of the DNA with restriction enzymes and subsequent ligation, if necessary.

In the method using conventional genetic engineering techniques of the item (2), the polynucleotide of the present invention may be produced, for example, by the following procedure.

First, single-stranded cDNA is synthesized by using reverse transcriptase from mRNA prepared by the above-mentioned PCR method as a template, and then double-stranded cDNA is synthesized from the single-stranded cDNA. As this method, there may be mentioned, for example, an S1 nuclease method (Efstratiadis, A. et al., Cell, 7, 279–288, 1976), a Land method (Land, H. et al., Nucleic Acids Res., 9, 2251–2266, 1981), an O. Joon Yoo method (Yoo, O. J. et al., Proc. Natl. Acad. Sci. USA, 79, 1049–1053, 1983), and an Okayama-Berg method (Okayama, H. and Berg, P., Mol. Cell. Biol., 2, 161–170, 1982).

Next, a recombinant plasmid comprising the double-stranded cDNA is prepared and introduced into an *Escherichia coli* strain, such as DH 5(, thereby transforming the strain. A transformant is selected using a drug resistance against, for example, tetracycline or ampicillin as a marker. When the host cell is *E. coli*, transformation of the host cell may be carried out, for example, by the method of Hanahan (Hanahan, D. J., Mol. Biol., 166, 557–580, 1983); namely, a method in which the recombinant DNA is added to competent cells prepared in the presence of CaCl2, MgCl2, or RbCl. Further, as a vector other than a plasmid, a phage vector such as a lambda system may be used.

As a method for selecting a transformant containing the cDNA of interest from the resulting transformants, various methods such as (i) a method for screening a transformant using a synthetic oligonucleotide probe, (ii) a method for screening a transformant using a probe produced by PCR, (iii) a method for screening a transformant using an antibody against the polypeptide of the present invention, or (iv) a method for screening a transformant on the basis of the background potassium channel activity, may be used.

In the method of the item (i) for screening a transformant using a synthetic oligonucleotide probe, the transformant containing the cDNA of interest may be selected, for example, by the following procedure.

An oligonucleotide which corresponds to the whole or a part of the polypeptide of the present invention is synthesized (in this case, it may be either a nucleotide sequence taking the codon usage into consideration or a plurality of nucleotide sequences as a combination of possible nucleotide sequences) and, using this oligonucleotide as a probe (labeled with $^{32}P$ or $^{33}P$), hybridized with a nitrocellulose filter on which DNAs of the transformants are denatured and fixed, to screen and select resulting positive strains.

In the method of the item (ii) for screening a transformant using a probe produced by PCR, the transformant containing the cDNA of interest may be selected, for example, by the following procedure.

Oligonucleotides of a sense primer and an antisense primer corresponding to a part of the polypeptide of the present invention are synthesized, and a DNA fragment encoding the whole or a part of the polypeptide of interest is amplified by carrying out PCR using these primers in combination. As a template DNA used in this method, cDNA synthesized by a reverse transcription reaction from mRNA of cells capable of producing the polypeptide of the present invention, or genomic DNA, may be used. The resulting DNA fragment is labeled with $^{32}P$ or $^{33}P$, and a transformant containing the cDNA of interest is selected by carrying out a colony hybridization or a plaque hybridization using this fragment as a probe.

In the method of the item (iii) for screening a transformant using an antibody against the polypeptide of the present invention, the transformant containing the cDNA of interest may be selected, for example, by the following procedure.

First, cDNA is integrated into an expression vector, and polypeptides are produced on the cell surface of transformants. A transformant containing the cDNA of interest is selected by detecting a strain producing the desired polypeptide using an antibody against the polypeptide of the present invention and a second antibody against the first antibody.

In the method of the item (iv) for screening a transformant on the basis of the background potassium channel activity, the transformant containing the cDNA of interest may be selected, for example, by the following procedure.

First, cDNA is integrated into an expression vector, and polypeptides are produced on the cell surface of transformants. A transformant containing the cDNA of interest is selected by detecting a strain producing the desired polypeptide on the basis of the background potassium channel activity.

A method for collecting the polynucleotide of the present invention from the resulting transformant of interest can be carried out in accordance with a known method (for example, Maniatis, T. et al., "Molecular Cloning—A Laboratory Manual", Cold Spring Harbor Laboratory, NY, 1982). For example, it may be carried out by separating a fraction corresponding to the plasmid DNA from cells and cutting out the cDNA region from the plasmid DNA.

In the chemical synthesis method of the item (3), the polynucleotide of the present invention may be produced, for example, by binding DNA fragments produced by a chemical synthesis method. Each DNA can be synthesized using a DNA synthesizer [for example, Oligo 1000M DNA Synthesizer (Beckman) or 394 DNA/RNA Synthesizer (Applied Biosystems)].

Further, the polynucleotide of the present invention may be produced by nucleic acid chemical synthesis in accordance with a conventional method such as a phosphate triester method (Hunkapiller, M. et al., Nature, 10, 105–111, 1984), based on the information on the polypeptide of the present invention. In this connection, codons for each amino acid are known and can be optionally selected and determined by the conventional method, for example, by taking a codon usage of each host to be used into consideration (Crantham, R. et al., Nucleic Acids Res., 9, r43–r 74, 1981). Further, a partial modification of codons of these base sequences can be carried out in accordance with a conventional method, such as site directed mutagenesis which uses a primer comprised of a synthetic oligonucleotide coding for a desired modification (Mark, D. F. et al., Proc. Natl. Acad. Sci. USA, 81, 5662–5666, 1984).

Determination of the DNA sequences obtained by the above-mentioned methods can be carried out by, for example, a Maxam-Gilbert chemical modification method (Maxam, A. M. and Gilbert, W., "Methods in Enzymology", 65, 499–559, 1980) or a dideoxynucleotide chain termination method (Messing, J. and Vieira, J., Gene, 19, 269–276, 1982).

[3] The Expression Vector and the Cell of the Present Invention

An isolated polynucleotide of the present invention is re-integrated into an appropriate vector DNA and a eucaryotic or procaryotic host cell may be transfected by the resulting expression vector. Further, it is possible to express the polynucleotide in a desired host cell, by introducing an appropriate promoter and a sequence related to the gene expression into the vector.

The expression vector of the present invention is not particularly limited, so long as it comprises the polynucleotide of the present invention. As the expression vector, there may be mentioned, for example, an expression vector obtained by introducing the polynucleotide of the present invention into a known expression vector appropriately selected in accordance with a host cell to be used.

The cell of the present invention is not particularly limited, so long as it is transfected with the expression vector of the present invention and comprises the polynucleotide of the present invention. The cell of the present invention may be, for example, a cell in which the polynucleotide is integrated into a chromosome of a host cell, or a cell containing the polynucleotide as an expression vector comprising polynucleotide. Further, the cell of the present invention may be a cell expressing the polypeptide of the present invention, or a cell not expressing the polypeptide of the present invention. The cell of the present invention may be obtained by, for example, transfecting a desired host cell with the expression vector of the present invention.

In the eucaryotic host cells, for example, cells of vertebrates, insects, and yeast are included. As the vertebral cell, there may be mentioned, for example, a simian COS cell (Gluzman, Y., Cell, 23, 175–182, 1981), a dihydrofolate reductase defective strain of a Chinese hamster ovary cell (CHO) (Urlaub, G. and Chasin, L. A., Proc. Natl. Acad. Sci. USA, 77, 4216–4220, 1980), a CHO-K1 cell used in Example 9, a human embryonic kidney derived HEK293 cell, a 293-EBNA cell (Invitrogen) obtained by introducing an EBNA-1 gene of Epstein Barr Virus into HEK293 cell, a L929 cell (ATCC: CRL-2148) used in Example 5, or the like.

As an expression vector for a vertebral cell, a vector containing a promoter positioned upstream of the gene to be expressed, an RNA splicing site, a polyadenylation site, a transcription termination sequence, and the like may be generally used. The vector may further contain a replication origin, if necessary. As the expression vector, there may be mentioned, for example, pSV2dhfr containing an SV40 early promoter (Subramani, S. et al., Mol. Cell. Biol., 1, 854–864, 1981)., pEF-BOS containing a human elongation factor promoter (Mizushima, S. and Nagata, S., Nucleic Acids Res., 18, 5322, 1990), pCEP4 containing a cytomegalovirus promoter (Invitrogen), pIRESneo2 (CLONTECH), or the like.

When the COS cell is used as the host cell, a vector which has an SV40 replication origin, can perform an autonomous replication in the COS cell, and has a transcription promoter, a transcription termination signal, and an RNA splicing site, may be used as the expression vector. As the vector, there may be mentioned, for example, pME18S (Maruyama, K. and Takebe, Y., Med. Immunol., 20, 27–32, 1990), pEF-BOS (Mizushima, S. and Nagata, S., Nucleic Acids Res., 18, 5322, 1990), or pCDM8 (Seed, B., Nature, 329, 840–842, 1987).

The expression vector may be incorporated into COS cells by, for example, a DEAE-dextran method (Luthman, H. and Magnusson, G., Nucleic Acids Res., 11, 1295–1308, 1983), a calcium phosphate-DNA co-precipitation method (Graham, F. L. and van der Ed, A. J., Virology, 52, 456–457, 1973), a method using a commercially available transfection reagent (for example, FuGENE™6 Transfection Reagent; Roche Diagnostics), or an electroporation method (Neumann, E. et al., EMBO J., 1, 841–845, 1982).

When the CHO cell is used as the host cell, a transfected cell capable of stably producing the polypeptide of the present invention can be obtained by carrying out co-transfection of an expression vector comprising the polynucleotide encoding the polypeptide of the present invention, together with a vector capable of expressing a neo gene which functions as a G418 resistance marker, such as pRSVneo (Sambrook, J. et al., "Molecular Cloning—A Laboratory Manual", Cold Spring Harbor Laboratory, NY, 1989) or pSV2-neo (Southern, P. J. and Berg, P., J. Mol. Appl. Genet., 1, 327–341, 1982), and selecting a G418 resistant colony.

When the 293-EBNA cell is used as the host cell, for example, pCEP4 (Invitrogen) containing a replication origin of Epstein Barr Virus and capable of performing an autonomous replication in the 293-EBNA cell may be used as the expression vector.

The cell of the present invention may be cultured in accordance with the conventional method [for example, "Shin Seikagaku Jikken Koza 18, Saibou Baiyou Gijyutsu (Japanese Biochemical Society)", Tokyo Kagaku Dojin, 1990], and the polypeptide of the present invention is produced in the cells or on the cell surface. As a medium to be used in the culturing, a medium commonly used in a desired host cell may be appropriately selected. In the case of the COS cell, for example, a medium such as an RPMI-1640 medium or a Dulbecco's modified Eagle's minimum essential medium (DMEM) may be used, by supplementing it with a serum component such as fetal bovine serum (FBS) if necessary. In the case of the 293-EBNA cell, a medium such as a Dulbecco's modified Eagle's minimum essential medium (DMEM) with a serum component such as fetal bovine serum (FBS) and G418 may be used.

The polypeptide of the present invention produced in the cells or on the cell surface of the present invention by culturing the cells may be separated and purified therefrom by various known separation techniques [for example, Okada, M. and Miyazaki K. "Kaitei, Tanpakushitsu Jikken Noto, Jyo•Ge (Revision, Notebook for Protein Experiments)", Yodo-sha 1999] making use of the physical properties, chemical properties and the like of the polypeptide. More particularly, for example, a cell membrane fraction containing the polypeptide of the present invention may be obtained by culturing the cell in which the polypeptide of the present invention is expressed on the surface thereof, suspending the cell in a buffer, homogenizing the suspension, and centrifuging the homogenate. The polypeptide of the present invention may be purified by solubilizing the resulting cell membrane fraction, and then by a treatment with a commonly used protein precipitant, ultrafiltration, various liquid chromatography techniques such as molecular sieve chromatography (gel filtration), adsorption chromatography, ion exchange chromatography, affinity chromatography, or high performance liquid chromatography (HPLC), or dialysis, or a combination thereof. In this connection, when the cell membrane fraction is solubilized using as mild as possible a solubilizing agent (such as CHAPS, Triton X-100, digitonin or the like), characteristics of the potassium channel may be maintained after the solubilization.

When the polypeptide of the present invention is expressed as a fusion protein with a marker sequence in frame, a confirmation of the expression of the polypeptide of the present invention, a confirmation of intracellular localization thereof, a purification thereof, or the like may be easily carried out. As the marker sequence, there may be mentioned, for example, a FLAG epitope, a hexa-histidine tag, a hemagglutinin tag, or a myc epitope. Further, by inserting a specific amino acid sequence recognized by a protease such as enterokinase, factor Xa, or thrombin between the marker sequence and the polypeptide of the present invention, the marker sequence may be removed by the protease. For example, there is a report in which a muscarinic acetylcholine receptor and a hexa-histidine tag were connected by a thrombin recognition sequence (Hayashi, M. K. and Haga, T., J. Biochem., 120, 1232–1238, 1996).

[4] The Detecting Method and Screening Method of the Present Invention

It is possible to detect whether or not a test compound suppresses the polypeptide of the present invention, using the cell of the present invention in which the polypeptide of the present invention is expressed. Further, it is possible to screen a substance suppressing the polypeptide of the present invention, using the detecting method of the present invention.

As previously described, the polypeptide of the present invention is a background potassium channel which is significantly expressed in the pancreas. A membrane potential in a cell is determined by the distribution of charges from inorganic ions such as $Na^+$, $K^+$, $Cl^-$, $Ca^{2+}$, or the like inside and outside of the cell. The charge distribution is changed by an opening and closing of various ion channels composed of membrane proteins. Therefore, the opening and closing of ion channels play an important role in the change of the membrane potential. In particular, it is considered that a potassium channel (a membrane protein which allows a potassium ion to selectively pass through) is involved with the maintenance of a resting membrane potential, the repolarization of a membrane potential after depolarization, or the like, and the potassium channel is a desirable target for controlling the excitation of cells. This shows that an agent for suppressing the potassium channel in cells shifts the membrane potential to the depolarization side, and has an activity which increases the excitation of cells.

The potassium channels are classified into a voltage-gated potassium channel, a $Ca^{2+}$-activated potassium channel, an ATP-sensitive potassium channel, an inward rectifier potassium channel, a background potassium channel, and the like, on the basis of their functions. Among the channels, the background potassium channel exhibits a property in which the channel is opened under the resting membrane potential, and thus it is considered that the background potassium channel largely contributes to the control of the resting membrane potential (Lesage, EMBO J., 15, 1004, 1996; and Duprat, EMBO J., 16, 5464, 1997). Suppression of the background potassium channel shifts the membrane potential to the depolarization side. For example, it is known that a current of background potassium ions in a cerebellar granule cell is suppressed by an extracellular acidification, and it is reported that the suppression shifts the membrane potential of the cell to the depolarization side (Millar, Proc. Natl. Acad. Sci. USA, 97, 3614–3618, 2000).

In pancreatic β cells, a shift of the membrane potential to the deolarization side causes insulin secretion (Henquin, J, Joslin's Diabetes Mellitus, 13th ed., Lea & Febiger, Pennsylvania, 56–80, 1994; Ashcroft, F. M., Insulin: Molecular Biology to Pathology, IRLpress, Oxford, 97–150, 1992). That is, it is considered that an agent increasing the excitation of the pancreatic β cells causes insulin secretion.

As described in Example 8, the polypeptide of the present invention shows properties of the background potassium channel under the same pH condition as that of the physiological conditions, and thus it is considered that the polypeptide of the present invention is involved with the maintenance of a resting membrane potential, the repolarization of a membrane, or the like. Therefore, it is considered that an agent for suppressing the polypeptide of the present invention is useful as a therapeutic agent for diabetes in which the mechanism is an increase in the excitation of pancreatic β cells and a promotion of insulin secretion.

Therefore, the cell of the present invention per se may be used as a screening tool for a therapeutic agent for diabetes (particularly an agent for suppressing the polypeptide of the present invention).

In this connection, to "suppress" the polypeptide of the present invention as used herein means to suppress the channel function of the polypeptide of the present invention, and includes suppressing the channel function by suppressing an expression of the polypeptide.

Compounds to be tested which may be applied to the detecting method or screening method of the present invention are not particularly limited, but there may be mentioned, for example, various known compounds (including peptides) registered in chemical files, compounds obtained by combinatorial chemistry techniques (Terrett, N. K. et al., Tetrahedron, 51, 8135–8137, 1995), or random peptides prepared by employing a phage display method (Felici, F. et al., J. Mol. Biol., 222, 301–310, 1991) or the like. In addition, culture supernatants of microorganisms, natural components derived from plants or marine organisms, or animal tissue extracts may be used as the test compounds for screening. Further, compounds (including peptides) obtained by chemically or biologically modifying compounds (including peptides) selected by the screening method of the present invention may be used.

The detecting method of the present invention comprises the steps of:
bringing the cell of the present invention into contact with a test compound, and
analyzing whether or not the polypeptide is suppressed.

The detecting method of the present invention is not particularly limited, so long as it comprises the steps of:
bringing the cell of the present invention expressing the polypeptide of the present invention as an effective background potassium channel (i.e., the cell which is transfected with an expression vector comprising the polynucleotide encoding the polypeptide of the present invention, and in which the polypeptide is expressed as an effective background potassium channel) into contact with a compound to be tested; and
analyzing whether or not the polypeptide is suppressed.

There may be mentioned, on the basis of differences in methods used for analyzing a suppression of the polypeptide of the present invention, for example,
(1) a detecting method utilizing a voltage-clamp method (particularly whole-cell voltage-clamp method,
(2) a detecting method utilizing a radioisotope rubidium ($^{86}Rb^+$) ion release, or
(3) a detecting method utilizing a voltage-sensitive dye.

Among these methods, the detecting method utilizing a radioisotope rubidium ($^{86}Rb^+$) ion release is preferable.

When detecting a substance which is useful as a therapeutic agent for diabetes and suppresses the polypeptide of the present invention utilizing the voltage-clamp method (particularly whole-cell voltage-clamp method) of the item (1), it is analyzed whether or not the polypeptide of the present invention is suppressed, by voltage-clamping the cell of the present invention expressing the polypeptide of the present invention on the cell surface by the voltage-clamp method (particularly whole-cell voltage-clamp method) and analyzing (i.e., measuring or detecting) a whole-cell current of the cell in the presence of a test compound. That is, the detecting method of the present invention utilizing the voltage-clamp method (particularly whole-cell voltage-clamp method) comprises the steps of:
bringing the cell of the present invention expressing the polypeptide of the present invention on the cell surface while voltage-clamping by the voltage-clamp method (particularly whole-cell voltage-clamp method), into contact with a test compound, and
analyzing a change of the whole-cell current in the cell.

More particularly, it is preferable to carry out the procedure by a method described in Example 6. For example, a solution containing 149 mol/L NaCl, 5 mmol/L KCl, 2 mmol/L $MgCl_2$, and 10 mmol/L HEPES-Na (pH=7.3) may be used as an extracellular solution, and a solution containing 149 mmol/L KCl, 1.8 mmol/L $MgCl_2$, 4.5 mmol/L EGTA, and 9 mmol/L HEPES-K (pH=7.3) may be used as an intracellular solution. For example, when a test compound is added to an extracellular solution of a voltage-clamped cell at a holding potential of −40 mV, and then an outward current is suppressed, it may be confirmed that the test compound is a substance which suppresses the polypeptide of the present invention.

When detecting a substance which is useful as a therapeutic agent for diabetes and suppresses the polypeptide of the present invention utilizing the radioisotope rubidium ($^{86}Rb^+$) ion release of the item (2), it is analyzed whether or not the polypeptide of the present invention is suppressed, by making the cell of the present invention expressing the polypeptide of the present invention on the cell surface incorporate the radioisotope rubidium ($^{86}Rb^+$) ion, and then analyzing (i.e., measuring or detecting) an amount of radioactivity released outside of the cell when a test compound is added (Maingret et al., J. Biol. Chem., 274, 1381, 1999). That is, the detecting method of the present invention utilizing the radioisotope rubidium ($^{86}Rb^+$) ion release comprises the steps of:

making the cell of the present invention expressing the polypeptide of the present invention on the cell surface incorporate the radioisotope rubidium ($^{86}Rb^+$) ion, and then bringing the cell into contact with a test compound, and analyzing an amount of radioactivity released outside of the cell. This detection utilizes a feature that a potassium channel generally allows rubidium ions, as well as potassium ions, to pass through.

More particularly, it is preferable to carry out the procedure by a method described in Example 10. For example, the rubidium ($^{86}Rb^+$) ions can be incorporated into the cell of the present invention expressing the polypeptide of the present invention on the cell surface by incubating the cell with $^{86}RbCl$. The cell is washed with a solution containing a common concentration (such as 2.5 mmol/L) of potassium ions to remove rubidium ions not incorporated. The cell is stimulated with a high concentration (such as 100 mmol/L) of potassium ions, and then the rubidium ($^{86}Rb^+$) ions are released from the cell. When the potassium channel is suppressed, the amount of the rubidium ($^{86}Rb^+$) ion released from the cell decreases. Therefore, it can be analyzed whether or not the polypeptide of the present invention is suppressed, on the basis of the radioactivity in the extracellular solution as the channel activity. A substance which suppresses the polypeptide of the present invention can be detected by analyzing (i.e., measuring or detecting) the radioactivity released outside of the cell when a test compound is added.

When detecting a substance which is useful as a therapeutic agent for diabetes and suppresses the polypeptide of the present invention utilizing the voltage-sensitive dye of the item (3), it is analyzed whether or not the polypeptide of the present invention is suppressed, by making the cell of the present invention expressing the polypeptide of the present invention on the cell surface incorporate the voltage-sensitive dye, and then analyzing (i.e., measuring or detecting) a change of a fluorescence intensity thereof in the cell when a test compound is added. That is, the detecting method of the present invention utilizing the voltage-sensitive dye comprises the steps of:

making the cell of the present invention expressing the polypeptide of the present invention on the cell surface incorporate the voltage-sensitive dye, and then bringing the cell into contact with a test compound, and analyzing a change of a fluorescence intensity thereof in the cell. This detection utilizes a feature that a change of a membrane potential by an opening of the potassium channel can be detected by the voltage-sensitive dye.

More particularly, DiBAC [bis-(1,3-dibutylbarbituric acid)trimethine oxbnol; manufactured by Molecular Probe] or a derivative thereof may be used as the voltage-sensitive dye. The activity of the polypeptide of the present invention can be analyzed (i.e., measured or detected) using these dyes, and a substance which suppresses the polypeptide of the present invention can be detected by comparing changes of the fluorescence intensity of the dye in the presence and absence of a test compound. More particularly, when the potassium channel is suppressed, the fluorescence intensity increases.

In the method of the present invention for screening a therapeutic agent for diabetes (particularly an agent for suppressing the polypeptide of the present invention), whether or not a test compound suppresses the polypeptide of the present invention using the detecting method of the present invention is detected, and then, on the basis of the result, a substance which suppresses the polypeptide of the present invention, or a therapeutic agent for diabetes, is selected. More particularly, for example, the cell of the present invention in which the polypeptide of the present invention is expressed is brought into contact with a test compound, and then a substance which suppresses the polypeptide of the present invention, or a therapeutic agent for diabetes can be selected, on the basis of a presence or absence of the suppression of the polypeptide or a degree of the suppression in the presence of the test compound, as a marker.

[5] The Antibody or the Fragment Thereof of the Present Invention

An antibody, such as a polyclonal antibody or a monoclonal antibody, which reacts with the polypeptide of the present invention may be obtained by directly administering the polypeptide of the present invention or a fragment thereof to various animals. Alternatively, it may be obtained by a DNA vaccine method (Raz, E. et al., Proc. Natl. Acad. Sci. USA, 91, 9519–9523, 1994; or Donnelly, J. J. et al., J. Infect. Dis., 173, 314–320, 1996), using a plasmid into which a polynucleotide encoding the polypeptide of the present invention is inserted.

The polyclonal antibody may be produced from a serum or eggs of an animal such as a rabbit, a rat, a goat, or a chicken, in which the animal is immunized and sensitized by the polypeptide of the present invention or a fragment thereof emulsified in an appropriate adjuvant (for example, Freund's complete adjuvant) by intraperitoneal, subcutaneous, or intravenous administration. The polyclonal antibody may be separated and purified from the resulting serum or eggs in accordance with conventional methods for polypeptide isolation and purification. Examples of the separation and purification methods include, for example, centrifugal separation, dialysis, salting-out with ammonium sulfate, or a chromatographic technique using such as DEAE-cellulose, hydroxyapatite, protein A agarose, and the like.

The monoclonal antibody may be easily produced by those skilled in the art, according to, for example, a cell fusion method of Kohler and Milstein (Kohler, G. and Milstein, C., Nature, 256, 495–497, 1975).

A mouse is immunized intraperitoneally, subcutaneously, or intravenously several times at an interval of a few weeks by a repeated inoculation of emulsions in which the polypeptide of the present invention or a fragment thereof is emulsified into a suitable adjuvant such as Freund's complete adjuvant. Spleen cells are removed after the final immunization, and then fused with myeloma cells to prepare hybridomas.

As a myeloma cell for obtaining a hybridoma, a myeloma cell having a marker such as a deficiency in hypoxanthine-guanine phosphoribosyltransferase or thymidine kinase (for example, mouse myeloma cell line P3X63Ag8.U1) may be used. As a fusing agent, polyethylene glycol may be used. As a medium for preparation of hybridomas, for example, a commonly used medium such as an Eagle's minimum essential medium, a Dulbecco's modified minimum essential medium, or an RPMI-1640 medium may be used by properly adding 10 to 30% of a fetal bovine serum. The fused strains may be selected by a HAT selection method. A culture supernatant of the hybridomas is screened by a well-known method such as an ELISA method or an immunohistological method, to select hybridoma clones secreting the antibody of interest. The monoclonality of the selected hybridoma is guaranteed by repeating subcloning by a limiting dilution method. Antibodies in an amount which may be purified are produced by culturing the resulting hybridomas in a medium for 2 to 4 days, or in the peritoneal cavity of a pristane-pretreated BALB/c strain mouse for 10 to 20 days.

The resulting monoclonal antibodies in the culture supernatant or the ascites may be separated and purified by conventional polypeptide isolation and purification methods. Examples of the separation and purification methods include, for example, centrifugal separation, dialysis, salting-out with ammonium sulfate, or chromatographic technique using such as DEAE-cellulose, hydroxyapatite, protein A agarose, and the like.

Further, the monoclonal antibodies or the antibody fragments containing a part thereof may be produced by inserting the whole or a part of a gene encoding the monoclonal antibody into an expression vector and introducing the resulting expression vector into appropriate host cells (such as E. coli, yeast, or animal cells).

Antibody fragments comprising an active part of the antibody such as $F(ab')_2$, Fab, Fab', or Fv may be obtained by a conventional method, for example, by digesting the separated and purified antibodies (including polyclonal antibodies and monoclonal antibodies) with a protease such as pepsin or papain, and separating and purifying the resulting fragments by standard polypeptide isolation and purification methods.

Further, an antibody which reacts to the polypeptide of the present invention may be obtained in a form of single chain Fv or Fab in accordance with a method of Clackson et al. or a method of Zebedee et al. (Clackson, T. et al., Nature, 352, 624–628, 1991; or Zebedee, S. et al., Proc. Natl. Acad. Sci. USA, 89, 3175–3179, 1992). Furthermore, a humanized antibody may be obtained by immunizing a transgenic mouse in which mouse antibody genes are substituted with human antibody genes (Lonberg, N. et al., Nature, 368, 856–859, 1994).

EXAMPLES

The present invention now will be further illustrated by, but is by no means limited to, the following Examples. The procedures were performed in accordance with the known methods (for example, Maniatis, T., et al., "Molecular Cloning—A Laboratory Manual", Cold Spring Harbor Laboratory, NY, 1982; and Hille, B., Ionic Channels of Excitable Membranes, 2nd Ed., Sinauer Associates Inc., MA, 1992), unless otherwise specified.

Example 1

Isolation of Human Gene Encoding Novel Potassium Channel and Construction of Expression Vector A full-length cDNA encoding the novel potassium channel of the present invention consisting of the amino acid sequence of SEQ ID NO: 2 was obtained by a reverse transcriptase-polymerase chain reaction (RT-PCR) using human pancreas poly $A^+$ RNA (Clontech) as a template by the following procedure.

First, a first-strand cDNA was synthesized by carrying out a reverse transcription from the human pancreas poly $A^+$ RNA (10 ng) as a template using a commercially available RT-PCR kit (SUPERSCRIPT First Strand Synthesis System for RT-PCR; GIBCO-BRL).

A PCR was carried out using the resulting first-strand cDNA as a template, the oligonucletide consisting of the base sequence of SEQ ID NO: 3 as a forward primed, the oligonucletide consisting of the base sequence of SEQ ID NO: 4 as a reverse primed, and DNA polymerase (PLATINUM Taq DNA Polymerase High-Fidelity; GIBCO-BRL). In the PCR, a thermal denaturation was first performed at 95° C. for 5 minutes, and then a cycle composed of treatments at 95° C. for 15 seconds and 68° C. for 2 minutes was repeated 35 times. As a result, a DNA fragment of approximately 0.9 kbp was amplified. The resulting DNA fragment was cloned using a commercially available cloning kit (TOPO XL PCR Cloning Kit; Invitrogen).

The resulting plasmid was digested with restriction enzymes SpeI and NotI, and a DNA fragment of approximately 0.9 kbp was purified. Independently of the purified DNA fragment, a plasmid pIRESneo2 (CLONTECH) was digested with restriction enzymes NheI and NotI, and a DNA fragment of approximately 5.5 kbp was purified and ligated to the previously purified DNA fragment of approximately 0.9 kbp, to obtain a plasmid pIRESneo2-hPSI. The plasmid pIRESneo2 contains a cytomegalovirus promoter sequence and may be used for an expression of the novel potassium channel in an animal cell.

The base sequence of the resulting clone pIRESneo2-hPSI was analyzed using a DNA sequencer (ABI377 DNA Sequencer; Applied Biosystems) by a dideoxy terminator method to obtain the base sequence of SEQ ID NO: 1.

The base sequence of SEQ ID NO: 1 contains an open reading frame consisting of 885 base pairs (a sequence consisting of the 13th to 897th bases in the base sequence of SEQ ID NO: 1). The amino acid sequence deduced from the open reading frame was the amino acid sequence of SEQ ID NO: 2 consisting of 294 amino acid residues.

Example 2

Isolation of Rat Gene Encoding Novel Potassium Channel and Construction of Expression Vector A full-length cDNA encoding the novel potassium channel of the present invention consisting of the amino acid sequence of SEQ ID NO: 6 was obtained by a reverse transcriptase-polymerase chain reaction (RT-PCR) using rat pancreas poly $A^+$ RNA (Clontech) as a template by the following procedure.

First, a first-strand cDNA was synthesized by carrying out a reverse transcription from the rat pancreas poly $A^+$ RNA (10 ng) as a template using a commercially available RT-PCR kit (SUPERSCRIPT First Strand Synthesis System for RT-PCR; GIBCO-BRL).

A PCR was carried out using the resulting first-strand cDNA as a template, the oligonucletide consisting of the base sequence of SEQ ID NO: 7 (having the XbaI recognition sequence added to the 5'-terminus) as a forward primed, the oligonucletide consisting of the base sequence of SEQ ID NO: 8 (having the EcoRI recognition sequence added to the 5'-terminus) as a reverse primed, and DNA polymerase (PLATINUM Taq DNA Polymerase High-Fidelity; GIBCO-BRL). In the PCR, a thermal denaturation was first performed at 95° C. for 5 minutes, and then a cycle composed of treatments at 95° C. for 15 seconds and 68° C. for 2 minutes was repeated 35 times. As a result, a DNA fragment of approximately 0.9 kbp was amplified.

The resulting DNA fragment was digested with restriction enzymes XbaI and EcoRI, and cloned into a plasmid pIRESneo2 (CLONTECH) to obtain a plasmid pIRESneo2-rPSI.

The base sequence of the resulting clone pIRESneo2-rPSI was analyzed using a DNA sequencer (ABI377 DNA Sequencer; Applied Biosystems) by a dideoxy terminator method to obtain the base sequence of SEQ ID NO: 5.

The base sequence of SEQ ID NO: 5 contains an open reading frame consisting of 879 base pairs (a sequence consisting of the 36th to 914th bases in the base sequence of SEQ ID NO: 5). The amino acid sequence deduced from the open reading frame was the amino acid sequence of SEQ ID NO: 6 consisting of 292 amino acid residues.

The amino acid sequence of SEQ ID NO: 6 has an 86.3% homology with that of SEQ ID NO: 2. The homology is a value obtained by the above-mentioned Clustal program.

Example 3

Isolation of Mouse Gene Encoding Novel Potassium Channel and Construction of Expression Vector A full-length cDNA encoding the novel potassium channel of the present invention consisting of the amino acid sequence of SEQ ID NO: 10 was obtained by a reverse transcriptase-polymerase chain reaction (RT-PCR) using mouse pancreas poly $A^+$ RNA (Clontech) as a template by the following procedure.

First, a first-strand cDNA was synthesized by carrying out a reverse transcription from the mouse pancreas poly $A^+$ RNA (10 ng) as a template using a commercially available RT-PCR kit (SUPERSCRIPT First Strand Synthesis System for RT-PCR; GIBCO-BRL).

A PCR was carried out using the resulting first-strand cDNA as a template, the oligonucletide consisting of the base sequence of SEQ ID NO: 11 (having the SpeI recognition sequence added to the 5'-terminus) as a forward primed, the oligonucletide consisting of the base sequence of SEQ ID NO: 12 (having the EcoRI recognition sequence added to the 5'-terminus) as a reverse primed, and DNA polymerase (PLATINUM Taq DNA Polymerase High-Fidelity; GIBCO-BRL). In the PCR, a thermal denaturation was first performed at 95° C. for 5 minutes, and then a cycle composed of treatments at 95° C. for 15 seconds and 68° C. for 2 minutes was repeated 35 times. As a result, a DNA fragment of approximately 0.9 kbp was amplified.

The resulting DNA fragment was digested with restriction enzymes SpeI and EcoRI, and cloned into a plasmid pIRESneo2 (CLONTECH) to obtain a plasmid pIRESneo2-mPSI.

The base sequence of the resulting clone pIRESneo2-mPSI was analyzed using a DNA sequencer (ABI377 DNA Sequencer; Applied Biosystems) by a dideoxy terminator method to obtain the base sequence of SEQ ID NO: 9.

The base sequence of SEQ ID NO: 9 contains an open reading frame consisting of 879 base pairs (a sequence consisting of the 1st to 879th bases in the base sequence of SEQ ID NO: 9). The amino acid sequence deduced from the open reading frame was the amino acid sequence of SEQ ID NO: 10 consisting of 292 amino acid residues.

The amino acid sequence of SEQ ID NO: 10 has an 87% homology and a 97.9% homology with those of SEQ ID NO: 2 and SEQ ID NO: 6, respectively. Each homology is a value obtained by the above-mentioned Clustal program.

Example 4

Analysis of Expression Distribution of Novel Potassium Channel Gene

An expression distribution of the gene encoding the novel potassium channel consisting of the amino acid sequence of SEQ ID NO: 2 in human tissues was analyzed by a RT-PCR method in accordance with the following procedure.

Poly $A^+$ RNA (5 ng, respectively; Clontech) from each human tissue was treated with DNase, and then a first-strand cDNA was synthesized by carrying out a reverse transcription using an RT-PCR kit (SUPERSCRIPT First Strand Synthesis System for RT-PCR; GIBCO-BRL).

A PCR was carried out using the resulting first-strand cDNA as a template, the oligonucletide consisting of the base sequence of SEQ ID NO: 3 as a forward primed, the oligonucletide consisting of the base sequence of SEQ ID NO: 4 as a reverse primed, and DNA polymerase (PLATINUM Taq DNA Polymerase; GIBCO-BRL). In the PCR, a thermal denaturation was first performed at 95° C. for 5 minutes, and then a cycle composed of treatments at 95° C. for 30 seconds and 68° C. for 2 minutes was repeated 30 times.

When the RT-PCR analysis of each human tissue (amygdala, caudate nucleus, hippocampus, corpus callosum, substantia nigra, thalamus, cerebellum, frontal lobe, hypothalamus, spinal cord, pituitary, whole brain, heart, placenta, lung, trachea, liver, skeletal muscle, kidney, pancreas, small intestine, stomach, spleen, bone marrow, thymus, thyroid, salivary gland, adrenal gland, mammary gland, and prostate) was carried out, a DNA fragment of approximately 0.9 kbp was strongly amplified in the pancreas and weakly in the stomach and small intestine.

Example 5

Expression of Novel Potassium Channel in Animal Cell L929 Cell

The novel potassium channel of the present invention consisting of the amino acid sequence of SEQ ID NO: 2, SEQ ID NO: 6, or SEQ ID NO: 10 was expressed in an animal cell to detect a channel activity of the protein. A L929 cell (ATCC: CRL-2148) in which a current from an endogenous channel is not generated by a change of its membrane potential was used as the animal cell. The L929 cell was transfected, using a commercially available transfection reagent (LipofectAMINE; GIBCO-BRL) and the expression vector pIRESneo2-hPSI obtained in Example 1, the expression vector pIRESneo2-rPSI obtained in Example 2, or the expression vector pIRESneo2-mPSI obtained in Example 3, to express the potassium channel in the cell. In this connection, the concrete procedure was carried out in accordance with a manual attached to the transfection reagent. Further, a cell transfected with the plasmid pIRESneo2 was prepared as a control cell in a similar fashion.

The resulting transfected cells were used in the following Examples 6 to 8.

Example 6

Detection of Channel Activity of Novel Potassium Channel

Each cell obtained in Example 5 was voltage-clamped by a whole-cell voltage-clamp method and a whole-cell current was measured. A solution containing 149 mmol/L NaCl, 5 mmol/L KCl, 2 mmol/L $MgCl_2$, and 10 mmol/L HEPES-Na (pH=7.3) was used as an extracellular solution, and a solution containing 149 mmol/L KCl, 1.8 mmol/L $MgCl_2$, 4.5 mmol/L EGTA, and 9 mmol/L HEPES-K (pH=7.3) as an intracellular solution.

When a depolarization pulse was given to the cell transfected with the plasmid pIRESneo2-hPSI, the plasmid pIRESneo2-rPSI, or the plasmid pIRESneo2-mPSI from a holding potential of −80 mV for 400 msec, an outward current was measured. This current was induced instantaneously and inactivation was not observed. These results accorded with properties of background potassium channels. By contrast, when the same depolarization pulse was given to the control cell, such a current was not observed.

Among the results, the result in the cell transfected with the plasmid pIRESneo2-hPSI is shown in FIG. 1. In FIG. 1, Graph (A) shows the result obtained by using the L929 cell transfected with the plasmid pIRESneo2-hPSI, and Graph (B) shows the result obtained by using the L929 cell transfected with the control vector (plasmid pIRESneo2).

Example 7

Confirmation of Selectivity of Potassium Ion by Novel Potassium Channel

To examine the selectivity of a potassium ion by the novel potassium channel of the present invention consisting of the amino acid sequence of SEQ ID NO: 2, SEQ ID NO: 6, or SEQ ID NO: 10, each reversal potential was measured using a voltage ramp, while changing a potassium ion concentration in the extracellular solution to 5 mmol/L, 15 mmol/L, 30 mmol/L, 75 mmol/L, and 150 mmol/L. As a result, when the potassium ion concentration was increased, the reversal potential was shifted to the depolarization side. The reversal potential in each potassium ion concentration was plotted and a linear regression was carried out. The slope was 52 mV/decade, which was close to the theoretical value of slope calculated from Nernst's equation. It is considered from this result that the novel potassium channel of the present invention consisting of the amino acid sequence of SEQ ID NO: 2, SEQ ID NO: 6, or SEQ ID NO: 10 exhibits a high selectivity of the potassium ion.

Example 8

Confirmation of pH Sensitivity of Novel Potassium Channel

An effect of an extracellular pH on the novel potassium channel of the present invention consisting of the amino acid sequence of SEQ ID NO: 2, SEQ ID NO: 6, or SEQ ID NO: 10 was examined. When the extracellular pH was gradually changed from 7.3 to an alkaline side, pH8.9 in the cell transfected with the plasmid pIRESneo2-hPSI, the plasmid pIRESneo2-rPSI, or the plasmid pIRESneo2-mPSI, the channel was activated in any membrane potential. By contrast, when the extracellular pH was gradually changed from 7.3 to an acid side, pH5.6, the channel was suppressed in any membrane potential. Further, each current value at 0 mV was plotted, as a relative value on the basis of the value at pH7.3, against each pH. As a result, saturation in the alkaline side was observed at approximately pH9 with an increase of 150%, and saturation in the acid side was observed at approximately pH6 with a suppression of 40%. A fitting of the plot was carried out with the Boltzmann equation to obtain pH7.2 as $P_{0.5}$ (half-maximal activity). As apparent from the results, it was confirmed that the novel potassium channel of the present invention consisting of the amino acid sequence of SEQ ID NO: 2, SEQ ID NO: 6, or SEQ ID NO: 10 has a high sensitivity to a change of the extracellular pH under physiological conditions.

Example 9

Expression of Novel Potassium Channel in Animal Cell CHO-K1

The procedure described in Example 5 was repeated, except that a CHO-K1 cell was used as an animal cell, to express the potassium channel in the cell. These resulting transfected cells were used in the following Example 10.

Example 10

Detection of Channel Activity of Novel Potassium Channel Utilizing Rubidium ($^{86}$Rb) Ion Release To conveniently measure the potassium channel activity, an ion permeability of the novel potassium channel of the present invention consisting of the amino acid sequence of SEQ ID NO: 2, SEQ ID NO: 6, or SEQ ID NO: 10 was examined by measuring a rubidium ion radioactivity in the novel potassium channel, on the basis of the feature that a potassium channel generally allows rubidium ions, as well as potassium ions, to pass through.

Each cell obtained in Example 9 was cultured in a culture liquid containing rubidium chloride ($^{86}$Rb chloride; 2 mCi/mL), and then rubidium ions were incorporated into the cell. Each cell was washed with a washing solution containing 150 mmol/L NaCl, 2.5 mmol/L KCl, 1.8 mmol/L $CaCl_2$, 0.8 mmol/L $MgCl_2$, and 5 mmol/L HEPES-Na (pH=7.4) to remove rubidium ions not incorporated, and replaced with a solution containing a high concentration of potassium ions (High K) [a solution containing 52.5 mmol/L NaCl, 100 mmol/L KCl, 1.8 mmol/L $CaCl_2$, 0.8 mmol/L $MgCl_2$, and 5 mmol/L HEPES-Na (pH=7.4)]. When a rubidium ion radioactivity contained in the High K solution was measured and analyzed by a liquid scintillation counter, the radioactivity was measured.

As a result, it is considered that the cell in which the novel potassium channel of the present invention is expressed allows rubidium ions to pass through due to a high potassium ion concentration stimulus (High K stimulus). It was confirmed in this system that the novel potassium channel of the present invention consisting of the amino acid sequence of SEQ ID NO: 2, SEQ ID NO: 6, or SEQ ID NO: 10 exhibits the potassium channel activity.

Example 11

Expression of Novel Potassium Channel in Animal Cell INS-1E

The novel potassium channel of the present invention consisting of the amino acid sequence of SEQ ID NO: 2 was expressed in a mouse pancreatic β cell strain (INS-1E; Danilo Janjic et al., Biochemical Pharmacology, 57, 639–648, 1999).

The INS-1E cells plated on a 24-well plate for cell culture were transfected, using a commercially available transfection reagent (LipofectAMINE2000; Invitrogen) and the expression vector pIRESneo2-hPSI obtained in Example 1, to express the potassium channel in the cells. The resulting cells were cultured in RPMI1640 containing 5% fetal bovine serum (FBS), 1 mmol/L pyruvic acid, 50 μmol/L 2-mercaptoethanol, and 10 mmol/L HEPES. In this connection, the concrete procedure was carried out in accordance with a manual attached to the transfection reagent.

INDUSTRIAL APPLICABILITY

The polypeptide of the present invention is a background potassium channel which is significantly expressed in the pancreas. Therefore, using the polypeptide of the present invention, a therapeutic agent for diabetes can be obtained by screening a substance for suppressing the polypeptide, and thus the polypeptide is useful.

Further, according to the cell of the present invention expressing the polypeptide of the present invention on the cell surface, a convenient screening system for the therapeutic agent for diabetes can be provided. Furthermore, the polynucleotide, expression vector, cell, and antibody of the present invention are useful in producing the polypeptide of the present invention.

FREE TEXT IN SEQUENCE LISTING

Features of "Artificial Sequence" are described in the numeric identifier <223> in the Sequence Listing. More particularly, each of the base sequences of SEQ ID NOS: 7, 8, 11, and 12 is an artificially synthesized primer sequence.

Although the present invention has been described with reference to specific embodiments, various changes and modifications obvious to those skilled in the art are possible without departing from the scope of the appended claims.

The invention claimed is:

1. An isolated polypeptide comprising the amino acid sequence of SEQ ID NO: 6 or SEQ ID NO: 10 and exhibiting a background potassium channel activity.

2. An isolated polypeptide consisting of the amino acid sequence of SEQ ID NO: 6 or SEQ ID NO: 10.

3. An isolated polynucleotide encoding the polypeptide according to claims 1 or 2.

4. An expression vector comprising the polynucleotide according to claim 3.

5. A cell transfected with the expression vector according to claim 4.

6. A method of screening agents to identify a therapeutic agent for the treatment of diabetes, comprising:
   bringing a cell into contact with a test compound, wherein the cell is transfected with an expression vector comprising a polynucleotide encoding a polypeptide selected from:
   (a) a polypeptide comprising the amino acid sequence of SEQ ID NO: 6 or SEQ ID NO: 10, and exhibiting a background potassium channel activity, and
   (b) a polypeptide consisting of the amino acid sequence of SEQ ID NO: 6 or SEQ ID NO: 10, and
   analyzing whether the test compound suppresses the polypeptide, wherein a test compound that suppresses the polypeptide is identified as a therapeutic agent for the treatment of diabetes.

7. A method of screening agents to identify a therapeutic agent for the treatment of diabetes, comprising:
   bringing a cell into contact with a test compound, wherein the cell is transfected with an expression vector comprising a polynucleotide encoding a polypeptide selected from:
   (a) a polypeptide comprising the amino acid sequence of SEQ ID NO: 2 and exhibiting a background potassium channel activity, and
   (b) a polypeptide consisting of the amino acid sequence of SEQ ID NO: 2, and
   analyzing whether the test compound suppresses the polypeptide, wherein a test compound that suppresses the polypeptide is identified as a therapeutic agent for the treatment of diabetes.

* * * * *

UNITED STATES PATENT AND TRADEMARK OFFICE
CERTIFICATE OF CORRECTION

| | | |
|---|---|---|
| PATENT NO. | : 7,211,406 B2 | Page 1 of 1 |
| APPLICATION NO. | : 10/451892 | |
| DATED | : May 1, 2007 | |
| INVENTOR(S) | : Hiromichi Yokoi et al. | |

It is certified that error appears in the above-identified patent and that said Letters Patent is hereby corrected as shown below:

On the title page, item (73), "Pharms" should read --Pharma--

Signed and Sealed this

Nineteenth Day of June, 2007

JON W. DUDAS
*Director of the United States Patent and Trademark Office*

SEQUENCE LISTING

```
<160> NUMBER OF SEQ ID NOS: 12

<210> SEQ ID NO 1
<211> LENGTH: 897
<212> TYPE: DNA
<213> ORGANISM: Homo sapiens
<220> FEATURE:
<221> NAME/KEY: CDS
<222> LOCATION: (13)..(897)

<400> SEQUENCE: 1
cctggccaca gc atg ccc agt gct ggg ctc tgc agc tgc tgg ggt ggc cgg        51
            Met Pro Ser Ala Gly Leu Cys Ser Cys Trp Gly Gly Arg
              1               5                  10 gtg ctg ccc ctg ctg ctg gcc tat gtc tgc tac ctg ctg ctc ggt gcc        99
Val Leu Pro Leu Leu Leu Ala Tyr Val Cys Tyr Leu Leu Leu Gly Ala
     15                  20                  25 act atc ttc cag ctg cta gag agg cag gcg gag gct cag tcc agg gac       147
Thr Ile Phe Gln Leu Leu Glu Arg Gln Ala Glu Ala Gln Ser Arg Asp
 30                  35                  40                  45 cag ttt cag ttg gag aag ctg cgc ttc ctg gag aac tac acc tgc ctg       195
Gln Phe Gln Leu Glu Lys Leu Arg Phe Leu Glu Asn Tyr Thr Cys Leu
                 50                  55                  60 gac cag tgg gcc atg gag cag ttt gtg cag gtc atc atg gaa gcc tgg       243
Asp Gln Trp Ala Met Glu Gln Phe Val Gln Val Ile Met Glu Ala Trp
             65                  70                  75 gtg aaa ggt gtg aac ccc aaa ggc aac tct acc aac ccc agc aac tgg       291
Val Lys Gly Val Asn Pro Lys Gly Asn Ser Thr Asn Pro Ser Asn Trp
         80                  85                  90 gac ttt ggc agc agt ttc ttc ttt gca ggc aca gtc gtc act acc ata       339
Asp Phe Gly Ser Ser Phe Phe Phe Ala Gly Thr Val Val Thr Thr Ile
     95                  100                 105
```

```
gga tat ggg aac ctg gca ccc agc aca gag gca ggt cag gtc ttc tgt      387
Gly Tyr Gly Asn Leu Ala Pro Ser Thr Glu Ala Gly Gln Val Phe Cys
110             115                 120                 125 gtc ttc tat gcc ctg ttg ggc atc ccg ctt aac gtg atc ttc ctc aac      435
Val Phe Tyr Ala Leu Leu Gly Ile Pro Leu Asn Val Ile Phe Leu Asn
                130                 135                 140 cac ctg ggc aca ggg ctg cgt gcc cat ctg gcc gcc att gaa aga tgg      483
His Leu Gly Thr Gly Leu Arg Ala His Leu Ala Ala Ile Glu Arg Trp
            145                 150                 155 gag gac cgt ccc agg cgc tcc cag gta ctg caa gtc ctg ggc ctg gct      531
Glu Asp Arg Pro Arg Arg Ser Gln Val Leu Gln Val Leu Gly Leu Ala
        160                 165                 170 ctg ttc ctg acc ctg ggg acg ctg gtc att ctc atc ttc cca ccc atg      579
Leu Phe Leu Thr Leu Gly Thr Leu Val Ile Leu Ile Phe Pro Pro Met
    175                 180                 185 gtc ttc agc cat gtg gag ggc tgg agc ttc agc gag ggc ttc tac ttt      627
Val Phe Ser His Val Glu Gly Trp Ser Phe Ser Glu Gly Phe Tyr Phe
190                 195                 200                 205 gct ttc atc act ctc agc acc att ggc ttt ggg gac tat gtt gtt ggc      675
Ala Phe Ile Thr Leu Ser Thr Ile Gly Phe Gly Asp Tyr Val Val Gly
                210                 215                 220 aca gac ccc agc aag cat tat atc tca gtg tat cgg agc ctg gca gcc      723
Thr Asp Pro Ser Lys His Tyr Ile Ser Val Tyr Arg Ser Leu Ala Ala
            225                 230                 235 atc tgg atc ctc ctg ggc ctg gcg tgg ctg gcg ctg atc ctc cca ctg      771
Ile Trp Ile Leu Leu Gly Leu Ala Trp Leu Ala Leu Ile Leu Pro Leu
        240                 245                 250 ggc ccc ctg ctt ctg cac aga tgc tgc cag ctc tgg ctg ctc agt agg      819
Gly Pro Leu Leu Leu His Arg Cys Cys Gln Leu Trp Leu Leu Ser Arg
    255                 260                 265 ggc ctc ggc gtc aag gat ggg gca gcc tct gac ccc agt ggg ctc ccc      867
Gly Leu Gly Val Lys Asp Gly Ala Ala Ser Asp Pro Ser Gly Leu Pro
270                 275                 280                 285 agg cct cag aag atc ccc atc tct gca tga                              897
Arg Pro Gln Lys Ile Pro Ile Ser Ala
                290                 295

<210> SEQ ID NO 2
<211> LENGTH: 294
<212> TYPE: PRT
<213> ORGANISM: Homo sapiens

<400> SEQUENCE: 2

Met Pro Ser Ala Gly Leu Cys Ser Cys Trp Gly Gly Arg Val Leu Pro
1               5                   10                  15

Leu Leu Leu Ala Tyr Val Cys Tyr Leu Leu Gly Ala Thr Ile Phe
                20                  25                  30

Gln Leu Leu Glu Arg Gln Ala Glu Ala Gln Ser Arg Asp Gln Phe Gln
            35                  40                  45

Leu Glu Lys Leu Arg Phe Leu Glu Asn Tyr Thr Cys Leu Asp Gln Trp
        50                  55                  60

Ala Met Glu Gln Phe Val Gln Val Ile Met Glu Ala Trp Val Lys Gly
65                  70                  75                  80

Val Asn Pro Lys Gly Asn Ser Thr Asn Pro Ser Asn Trp Asp Phe Gly
                85                  90                  95

Ser Ser Phe Phe Phe Ala Gly Thr Val Val Thr Thr Ile Gly Tyr Gly
                100                 105                 110

Asn Leu Ala Pro Ser Thr Glu Ala Gly Gln Val Phe Cys Val Phe Tyr
```

```
                    115                 120                 125
Ala Leu Leu Gly Ile Pro Leu Asn Val Ile Phe Leu Asn His Leu Gly
        130                 135                 140

Thr Gly Leu Arg Ala His Leu Ala Ala Ile Glu Arg Trp Glu Asp Arg
145                 150                 155                 160

Pro Arg Arg Ser Gln Val Leu Gln Val Leu Gly Leu Ala Leu Phe Leu
                165                 170                 175

Thr Leu Gly Thr Leu Val Ile Leu Ile Phe Pro Met Val Phe Ser
            180                 185                 190

His Val Glu Gly Trp Ser Phe Ser Glu Gly Phe Tyr Phe Ala Phe Ile
            195                 200                 205

Thr Leu Ser Thr Ile Gly Phe Gly Asp Tyr Val Val Gly Thr Asp Pro
        210                 215                 220

Ser Lys His Tyr Ile Ser Val Tyr Arg Ser Leu Ala Ala Ile Trp Ile
225                 230                 235                 240

Leu Leu Gly Leu Ala Trp Leu Ala Leu Ile Leu Pro Leu Gly Pro Leu
                245                 250                 255

Leu Leu His Arg Cys Cys Gln Leu Trp Leu Leu Ser Arg Gly Leu Gly
            260                 265                 270

Val Lys Asp Gly Ala Ala Ser Asp Pro Ser Gly Leu Pro Arg Pro Gln
275                 280                 285

Lys Ile Pro Ile Ser Ala
        290
```

<210> SEQ ID NO 3
<211> LENGTH: 22
<212> TYPE: DNA
<213> ORGANISM: Homo sapiens

<400> SEQUENCE: 3
cctggccaca gcatgcccag tg                                        22

<210> SEQ ID NO 4
<211> LENGTH: 26
<212> TYPE: DNA
<213> ORGANISM: Homo sapiens

<400> SEQUENCE: 4
ttcatgcaga gatggggatc ttctga                                    26

<210> SEQ ID NO 5
<211> LENGTH: 914
<212> TYPE: DNA
<213> ORGANISM: Rattus sp.
<220> FEATURE:
<221> NAME/KEY: CDS
<222> LOCATION: (36)..(914)

<400> SEQUENCE: 5

```
caccctgaca accgctgcag agtcctggcc acatc atg ccc cgt gct ggg gtc        53
                                     Met Pro Arg Ala Gly Val
                                       1               5 tgc agc tgc tgg ggt ggc caa gta ttg ccc cta ctt ctg gcc tat atc      101
Cys Ser Cys Trp Gly Gly Gln Val Leu Pro Leu Leu Leu Ala Tyr Ile
            10                  15                  20 tgc tac ctg ctg ctt ggg gcc acc atc ttc cag cgg ctg gag aag cag      149
Cys Tyr Leu Leu Leu Gly Ala Thr Ile Phe Gln Arg Leu Glu Lys Gln
        25                  30                  35 gca gag gct cag tcc agg gac cag ttc cag ctg gaa aaa ctg cgc ttc      197
Ala Glu Ala Gln Ser Arg Asp Gln Phe Gln Leu Glu Lys Leu Arg Phe
```

```
                40                  45                  50
tta gag aac tac acc tgc ctg gac cag cag gcc ctg gag cag ttc gta      245
Leu Glu Asn Tyr Thr Cys Leu Asp Gln Gln Ala Leu Glu Gln Phe Val
 55                  60                  65                  70 cag gtc atc ctg gaa gcc tgg gtg aaa ggt gtg aac ccc aaa ggc aac      293
Gln Val Ile Leu Glu Ala Trp Val Lys Gly Val Asn Pro Lys Gly Asn
                 75                  80                  85 tcc acc aac ccc agc aac tgg gac ttc ggg agc agt ttc ttc ttt gca      341
Ser Thr Asn Pro Ser Asn Trp Asp Phe Gly Ser Ser Phe Phe Phe Ala
             90                  95                 100 ggc aca gtg gtc act acc ata ggt tat gga aac ctg gca ccc agc acg      389
Gly Thr Val Val Thr Thr Ile Gly Tyr Gly Asn Leu Ala Pro Ser Thr
            105                 110                 115 gag gca ggg cag gtc ttc tgt gtc ttc tat gcc ctg atg gga atc cca      437
Glu Ala Gly Gln Val Phe Cys Val Phe Tyr Ala Leu Met Gly Ile Pro
        120                 125                 130 ctc aac gtg gtc ttt ctc aac cat ctg ggc aca ggg ctg cgt gcc cat      485
Leu Asn Val Val Phe Leu Asn His Leu Gly Thr Gly Leu Arg Ala His
135                 140                 145                 150 ctg acc aca ctg gac agg tgg gag gac cac ccc agg cat tcc cag ctc      533
Leu Thr Thr Leu Asp Arg Trp Glu Asp His Pro Arg His Ser Gln Leu
                155                 160                 165 ctg cag gtc ctg ggc ctg gct ctg ttc ctg acc ttg ggg acc ctg gtc      581
Leu Gln Val Leu Gly Leu Ala Leu Phe Leu Thr Leu Gly Thr Leu Val
            170                 175                 180 att ctc atc ttc ccg ccc atg ttc ttc agc cac gtg gag ggc tgg agc      629
Ile Leu Ile Phe Pro Pro Met Phe Phe Ser His Val Glu Gly Trp Ser
        185                 190                 195 ttc cgt gag ggc ttc tac ttc gcc ttc atc acc ctc agc acc att ggc      677
Phe Arg Glu Gly Phe Tyr Phe Ala Phe Ile Thr Leu Ser Thr Ile Gly
    200                 205                 210 ttc ggg gac tat gtt gtc ggc aca gac ccc agc aag cac tac att gcg      725
Phe Gly Asp Tyr Val Val Gly Thr Asp Pro Ser Lys His Tyr Ile Ala
215                 220                 225                 230 gtg tat cgg agc ttg gca gct ata tgg atc ctc ctg ggc ctg gcg tgg      773
Val Tyr Arg Ser Leu Ala Ala Ile Trp Ile Leu Leu Gly Leu Ala Trp
                235                 240                 245 ctg gca gtg gtc ctc agc ttg gga tcc ctg ctt ctg cac agg tgc tcc      821
Leu Ala Val Val Leu Ser Leu Gly Ser Leu Leu Leu His Arg Cys Ser
            250                 255                 260 cgg ctc tgg cag ctt atc cga ggc ctg gac gtt aag gac cga gca gcc      869
Arg Leu Trp Gln Leu Ile Arg Gly Leu Asp Val Lys Asp Arg Ala Ala
        265                 270                 275 ccg ggc tct gag ccc aga tca cag aaa atc ccc ttc tct gca tga          914
Pro Gly Ser Glu Pro Arg Ser Gln Lys Ile Pro Phe Ser Ala
    280                 285                 290

<210> SEQ ID NO 6
<211> LENGTH: 292
<212> TYPE: PRT
<213> ORGANISM: Rattus sp.

<400> SEQUENCE: 6

Met Pro Arg Ala Gly Val Cys Ser Cys Trp Gly Gly Gln Val Leu Pro
 1               5                  10                  15

Leu Leu Leu Ala Tyr Ile Cys Tyr Leu Leu Gly Ala Thr Ile Phe
                20                  25                  30

Gln Arg Leu Glu Lys Gln Ala Glu Ala Gln Ser Arg Asp Gln Phe Gln
            35                  40                  45
```

```
Leu Glu Lys Leu Arg Phe Leu Glu Asn Tyr Thr Cys Leu Asp Gln Gln
 50                  55                  60

Ala Leu Glu Gln Phe Val Gln Val Ile Leu Glu Ala Trp Val Lys Gly
 65                  70                  75                  80

Val Asn Pro Lys Gly Asn Ser Thr Asn Pro Ser Asn Trp Asp Phe Gly
                 85                  90                  95

Ser Ser Phe Phe Phe Ala Gly Thr Val Val Thr Thr Ile Gly Tyr Gly
            100                 105                 110

Asn Leu Ala Pro Ser Thr Glu Ala Gly Gln Val Phe Cys Val Phe Tyr
        115                 120                 125

Ala Leu Met Gly Ile Pro Leu Asn Val Val Phe Leu Asn His Leu Gly
    130                 135                 140

Thr Gly Leu Arg Ala His Leu Thr Thr Leu Asp Arg Trp Glu Asp His
145                 150                 155                 160

Pro Arg His Ser Gln Leu Leu Gln Val Leu Gly Leu Ala Leu Phe Leu
                165                 170                 175

Thr Leu Gly Thr Leu Val Ile Leu Ile Phe Pro Pro Met Phe Phe Ser
            180                 185                 190

His Val Glu Gly Trp Ser Phe Arg Glu Gly Phe Tyr Phe Ala Phe Ile
        195                 200                 205

Thr Leu Ser Thr Ile Gly Phe Gly Asp Tyr Val Val Gly Thr Asp Pro
    210                 215                 220

Ser Lys His Tyr Ile Ala Val Tyr Arg Ser Leu Ala Ala Ile Trp Ile
225                 230                 235                 240

Leu Leu Gly Leu Ala Trp Leu Ala Val Val Leu Ser Leu Gly Ser Leu
                245                 250                 255

Leu Leu His Arg Cys Ser Arg Leu Trp Gln Leu Ile Arg Gly Leu Asp
            260                 265                 270

Val Lys Asp Arg Ala Ala Pro Gly Ser Glu Pro Arg Ser Gln Lys Ile
        275                 280                 285

Pro Phe Ser Ala
    290

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 7
ctctagagat catgccccgt gctg                                          24

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 8
ggaattcctc atgcagagaa ggggatttt                                     28

<210> SEQ ID NO 9
<211> LENGTH: 879
<212> TYPE: DNA
<213> ORGANISM: Mus sp.
```

```
<220> FEATURE:
<221> NAME/KEY: CDS
<222> LOCATION: (1)..(879)

<400> SEQUENCE: 9 atg ccc cgt gct ggg gtc tgc ggc tgc tgg ggt ggc caa gta ttg ccc      48
Met Pro Arg Ala Gly Val Cys Gly Cys Trp Gly Gly Gln Val Leu Pro
1               5                   10                  15 ctt ctt ctg gcc tat atc tgc tac cta ctg ctt ggg gcc acc atc ttc      96
Leu Leu Leu Ala Tyr Ile Cys Tyr Leu Leu Leu Gly Ala Thr Ile Phe
            20                  25                  30 cag ctg ctg gag aag cag gca gag gct caa tcc agg gac cag ttc cag     144
Gln Leu Leu Glu Lys Gln Ala Glu Ala Gln Ser Arg Asp Gln Phe Gln
        35                  40                  45 ctg gaa aag cta cgc ttc tta gag aac tac acc tgc cta gac cag cag     192
Leu Glu Lys Leu Arg Phe Leu Glu Asn Tyr Thr Cys Leu Asp Gln Gln
    50                  55                  60 gcc ctg gag cag ttt gta cag gtc atc ctg gaa gcc tgg gtg aag ggt     240
Ala Leu Glu Gln Phe Val Gln Val Ile Leu Glu Ala Trp Val Lys Gly
65                  70                  75                  80 gtg aac ccc aaa ggc aac tcc acc aat ccc agc aac tgg gac ttc ggg     288
Val Asn Pro Lys Gly Asn Ser Thr Asn Pro Ser Asn Trp Asp Phe Gly
                85                  90                  95 agc agc ttc ttc ttt gca ggc aca gtg gtc acc acc ata ggt tat gga     336
Ser Ser Phe Phe Phe Ala Gly Thr Val Val Thr Thr Ile Gly Tyr Gly
            100                 105                 110 aac ctg gcc ccc agc acg gag gca ggg cag gtc ttc tgt gtc ttc tat     384
Asn Leu Ala Pro Ser Thr Glu Ala Gly Gln Val Phe Cys Val Phe Tyr
        115                 120                 125 gct ctg atg ggg atc cca ctc aat gtg gtc ttc ctc aac cat ctg ggc     432
Ala Leu Met Gly Ile Pro Leu Asn Val Val Phe Leu Asn His Leu Gly
    130                 135                 140 aca ggg ctg cgg gcc cac ctg acc aca ttg gac agg tgg gag gac cac     480
Thr Gly Leu Arg Ala His Leu Thr Thr Leu Asp Arg Trp Glu Asp His
145                 150                 155                 160 ccc agg cat tcc cag ctc ctg cag gtc ctg ggc ctg gct ctg ttc ctg     528
Pro Arg His Ser Gln Leu Leu Gln Val Leu Gly Leu Ala Leu Phe Leu
                165                 170                 175 acc ttg ggg acc ctg gtc att ctc atc ttc cca ccc atg ttc ttc agc     576
Thr Leu Gly Thr Leu Val Ile Leu Ile Phe Pro Pro Met Phe Phe Ser
            180                 185                 190 cac gtg gag ggc tgg agc ttc cgt gag ggc ttc tac ttc gcg ttt atc     624
His Val Glu Gly Trp Ser Phe Arg Glu Gly Phe Tyr Phe Ala Phe Ile
        195                 200                 205 acc ctc agc acc att ggc ttc ggg gac tat gtt gtt ggc aca gac ccc     672
Thr Leu Ser Thr Ile Gly Phe Gly Asp Tyr Val Val Gly Thr Asp Pro
    210                 215                 220 agc aag cat tac atc gct gtg tat cgg agc ttg gca gct ata tgg atc     720
Ser Lys His Tyr Ile Ala Val Tyr Arg Ser Leu Ala Ala Ile Trp Ile
225                 230                 235                 240 ctc cta gga ctg gca tgg ctg gcg gtg gtc ctc agc ctg gga tcc ctg     768
Leu Leu Gly Leu Ala Trp Leu Ala Val Val Leu Ser Leu Gly Ser Leu
                245                 250                 255 ctt ctg cac agg tgc tcc cgg ctc tgg cag ctc atc aga ggc ctg gac     816
Leu Leu His Arg Cys Ser Arg Leu Trp Gln Leu Ile Arg Gly Leu Asp
            260                 265                 270 ctt aag gat gga gca gcc cct gac tct gag cct aga tca cag aaa atc     864
Leu Lys Asp Gly Ala Ala Pro Asp Ser Glu Pro Arg Ser Gln Lys Ile
        275                 280                 285 ccc atc tct gca tga                                                 879
Pro Ile Ser Ala
```

Pro Ile Ser Ala
    290

<210> SEQ ID NO 10
<211> LENGTH: 292
<212> TYPE: PRT
<213> ORGANISM: Mus sp.

<400> SEQUENCE: 10

Met Pro Arg Ala Gly Val Cys Gly Cys Trp Gly Gly Gln Val Leu Pro
1               5                   10                  15

Leu Leu Leu Ala Tyr Ile Cys Tyr Leu Leu Gly Ala Thr Ile Phe
            20                  25                  30

Gln Leu Leu Glu Lys Gln Ala Glu Ala Gln Ser Arg Asp Gln Phe Gln
            35                  40                  45

Leu Glu Lys Leu Arg Phe Leu Glu Asn Tyr Thr Cys Leu Asp Gln Gln
50                  55                  60

Ala Leu Glu Gln Phe Val Gln Val Ile Leu Glu Ala Trp Val Lys Gly
65                  70                  75                  80

Val Asn Pro Lys Gly Asn Ser Thr Asn Pro Ser Asn Trp Asp Phe Gly
            85                  90                  95

Ser Ser Phe Phe Phe Ala Gly Thr Val Val Thr Thr Ile Gly Tyr Gly
            100                 105                 110

Asn Leu Ala Pro Ser Thr Glu Ala Gly Gln Val Phe Cys Val Phe Tyr
            115                 120                 125

Ala Leu Met Gly Ile Pro Leu Asn Val Val Phe Leu Asn His Leu Gly
            130                 135                 140

Thr Gly Leu Arg Ala His Leu Thr Thr Leu Asp Arg Trp Glu Asp His
145                 150                 155                 160

Pro Arg His Ser Gln Leu Leu Gln Val Leu Gly Leu Ala Leu Phe Leu
                165                 170                 175

Thr Leu Gly Thr Leu Val Ile Leu Ile Phe Pro Pro Met Phe Phe Ser
            180                 185                 190

His Val Glu Gly Trp Ser Phe Arg Glu Gly Phe Tyr Phe Ala Phe Ile
            195                 200                 205

Thr Leu Ser Thr Ile Gly Phe Gly Asp Tyr Val Val Gly Thr Asp Pro
210                 215                 220

Ser Lys His Tyr Ile Ala Val Tyr Arg Ser Leu Ala Ala Ile Trp Ile
225                 230                 235                 240

Leu Leu Gly Leu Ala Trp Leu Ala Val Val Leu Ser Leu Gly Ser Leu
            245                 250                 255

Leu Leu His Arg Cys Ser Arg Leu Trp Gln Leu Ile Arg Gly Leu Asp
            260                 265                 270

Leu Lys Asp Gly Ala Ala Pro Asp Ser Glu Pro Arg Ser Gln Lys Ile
            275                 280                 285

Pro Ile Ser Ala
    290

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 11

```
gactagtcat catgccccgt gctgg                                              25

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 12
ggaattcctc atgcagagat ggggattt                                           28
```